United States Patent [19]
Bouniot et al.

[11] 3,990,943
[45] Nov. 9, 1976

[54] PROCESS FOR THE ENZYMATIC ISOMERIZATION OF GLUCOSE TO LEVULOSE

[75] Inventors: Albert Bouniot; Michel Guerineau, both of Deux Sevres, France

[73] Assignee: Rhone-Poulenc S.A., Paris, France

[22] Filed: Sept. 25, 1974

[21] Appl. No.: 509,345

[30] Foreign Application Priority Data
Sept. 27, 1973 France .................. 73.34649

[52] U.S. Cl. ............................. 195/31 F; 195/63; 195/68; 195/DIG. 11
[51] Int. Cl.² ....................................... C12D 13/02
[58] Field of Search ....... 195/31 F, 63, 68, DIG. 11; 210/38, 24

[56] References Cited
UNITED STATES PATENTS

| | | | |
|---|---|---|---|
| 2,676,922 | 4/1954 | Waisbrot | 210/38 |
| 3,708,397 | 1/1973 | Sipos | 195/31 F |
| 3,715,276 | 2/1973 | Takasaki et al. | 195/31 F |
| 3,788,945 | 1/1974 | Thompson et al. | 195/31 F |
| 3,834,940 | 9/1974 | Khaleeluddin et al. | 195/31 F |
| 3,868,304 | 2/1975 | Messing | 195/31 F |

FOREIGN PATENTS OR APPLICATIONS 1,959,169   6/1970   Germany ..................... 195/DIG. 11

OTHER PUBLICATIONS

Barker et al., "Enzyme Reactors for Industry," *Process Biochemistry*, Oct. 1971, vol. 6, No. 10, pp. 11–13.

*Primary Examiner*—A. Louis Monacell
*Assistant Examiner*—Thomas G. Wiseman
*Attorney, Agent, or Firm*—Cushman, Darby & Cushman

[57]         ABSTRACT

A process for the enzymatic isomerization of glucose to fructose where the glucose isomerase is combined with magnesium or magnesium and cobalt ions which have been fixed to a cation exchange resin. The glucose isomerase remains combined with the metal ions during the isomerization. The use of the instant complex prolongs the working life of the enzyme and minimizes the need for conventional pH control.

7 Claims, No Drawings

PROCESS FOR THE ENZYMATIC ISOMERIZATION OF GLUCOSE TO LEVULOSE

The present invention relates to the enzymatic isomerisation of glucose to levulose (fructose).

The isomerisation of glucose to levulose by contact with a suitable enzyme, usually originating from a micro-organism, is well known. In general, the isomerisation is carried out by introducing the enzyme into a solution, usually aqueous, of glucose at 50° to 75° C. This solution contains small amounts of one or more metal salts, especially magnesium salts and/or cobalt salts which provide activating magnesium and/or cobalt ions. The optimum pH for the isomerisation is about 8, but the pH tends to decrease during the reaction. In order to maintain the pH at its optimum value a solution of a base or a suitable buffer may be added. Alternatively, an insoluble or sparingly soluble compound which can counteract the acidity formed, such as an anion exchange resin or an alkaline earth metal carbonate, may be added to the solution.

It has now been found that the presence of the activating cation or cations mentioned above is essential for achieving a long working life for the enzyme. Further, when the activating cations are fixed to a cation exchanger, the enzyme remains combined with the activating cations, and the pH of the reaction medium need no longer be controlled as in the known processes.

Accordingly the present invention provides a process for isomerising glucose to levulose which comprises treating a solution, preferably an aqueous solution, of glucose with glucose isomerase in the presence of an activating cation (magnesium or magnesium and cobalt) which is fixed to a support consisting of a cation exchanger.

The cation exchanger is preferably a resin carrying sulphonic acid groups or carboxylic acid groups. The primary activating ion is the magnesium cation. The resin, initially in the acid form, is thus preferably saturated beforehand with magnesium hydroxide. When a $Mg^{++}$ and $Co^{++}$ ion-containing resin is to be used, once the resin has been saturated with magnesium hydroxide, it is contacted with a cobalt ion-containing solution which may contain $Co^{++}$ cations or $Co^{++}$ and $Mg^{++}$ cations. Although the utility of the invention does not depend on this theory, it appears probable that the surface of the resin carries $-SO_3Mg(OH)$ groups (in the case of the sulphonic acid resins) or $-COO-Mg(OH)$ groups (in the case of the carboxylic acid resins). The excess magnesium hydroxide is then removed by washing the resin with water saturated with magnesium carbonate in order to avoid eluting the fixed $Mg^{++}$ ions. The resulting resin is then preferably drained. The enzyme, or the remains of cells of a micro-organism containing the enzyme, is then mixed with the treated ion exchanger. The resulting composition may be placed in a column through which the aqueous solution of glucose is passed continuously. The concentration of this solution of glucose preferably does not exceed 60% by weight. The isomerisation reaction is carried out at a temperature of 50° to 75° C. The pH of the solution on issuing from the column is 5.0 to 6.5. The solution of glucose introduced can itself contain activating cations (especially $Mg^{++}$ and $Co^{++}$) in the amounts usually employed for this type of reaction, namely 2 to 200 parts per million (ppm) of $Mg^{++}$ cations and 1 to 100 ppm of $Co^{++}$ cations. The presence of $Mg^{++}$ ions in the glucose solution limits the elution of the active $Mg^{++}$ ions fixed to the support.

The degree of conversion of glucose in the issuing solution depends on the flow rate of the solution through the column, the limit given by the chemical equilibrium being of the order of 50% for the ratio glucose/glucose + levulose.

The following Examples illustrate the invention.

EXAMPLE 1

Experiment A 30 ml of a cation-exchange resin possessing carboxylic acid groups (Amberlite IRC 50 resin of Messrs. Rohm & Haas) are activated by treatment with hydrochloric acid, and then washed with distilled water. The resin is then contacted for 1 hour with 60 ml of a 15% solution of milk of magnesia (magnesium hydroxide), after which the excess milk of magnesia is removed by washing the resin copiosuly with water saturated with magnesium carbonate.

The resin thus obtained is drained and mixed with 565 mg of glucose isomerase (Nagase), corresponding to 1,960 G.I.U. The mixture is introduced into a vertical glass column of internal diameter 25 mm, which is surrounded by a jacket through which water, thermostatically controlled at 60° C, flows.

3 ml/hour of an aqueous solution containing 30% by weight of glucose, which also contains 0.26 g of $CoCl_2$ per liter and 0.10 g of $MgCO_3$ per liter, are passed through the column filled with treated resin and enzyme. The pH of the solution as it issues from the column is approximately 5.7 and the degree of conversion of glucose to levulose is 43%.

After 500 hours of operation, the results are the same. After 1,500 hours of operation under the same conditions the degree of conversion is still 22%.

Experiment B

By way of comparison, Experiment A was repeated but no enzyme was mixed with the resin. Only a 1% conversion of glucose to levulose was obtained. The pH of the solution as it issues from the column is 5.5.

It is apparent from this experiment that the process according to the invention indeed relates to an enzymatic reaction and not to a chemical reaction.

EXAMPLE 2

Experiment A of Example 1 was repeated except that 30 ml of a cation exchange resin possessing sulphonic acid groups (Allassion CS) activated by treatment with hydrochloric acid were used as the support.

From the beginning of the experiment onwards, a degree of conversion of glucose to levulose of 45% is achieved. A 43% conversion is still obtained after 300 hours of operation. Thereafter, the reaction rate decreases more quickly than in Experiment A of Example 1.

The pH of the solution as it issues from the reaction column is between 5 and 5.5.

We claim:

1. In a process for the isomerisation of glucose to levulose which comprises treating an aqueous solution of glucose with a glucose isomerase in the presence of the activating cations $Mg^{++}$ or $Mg^{++}$ and $Co^{++}$, the improvement which consists in contacting a cation exchanger, having $Mg^{++}$ or $Mg^{++}$ and $Co^{++}$ cations fixed thereto, with the glucose isomerase so that the said glucose isomerase becomes combined with the said fixed cations, and then treating the aqueous solution of glucose with the said combined glucose isomerase.

2. The improvement of claim 1, in which said cation exchanger is a cation exchange resin carrying sulphonic acid groups or carboxylic acid groups.

3. The improvement of claim 2, in which said resin, initially in the acid form, is saturated with magnesium hydroxide, and then washed with a saturated aqueous solution of magnesium carbonate, before being mixed with the glucose isomerase or the remains of cells of a micro-organism containing glucose isomerase.

4. The improvement of claim 1, in which the concentration of the solution of glucose does not exceed 60% by weight.

5. The improvement of claim 1, in which the solution of glucose contains $Mg^{++}$ or $Mg^{++}$ and $Co^{++}$ cations.

6. The improvement of claim 5, in which the solution of glucose contains about 2 to about 200 ppm of $Mg^{++}$ cations and about 1 to about 100 ppm of $Co^{++}$ cations.

7. The improvement of claim 1, in which the isomerisation is carried out at a temperature of about 50° to about 75° C.

* * * * *